United States Patent
Piterski et al.

(10) Patent No.: US 6,780,825 B2
(45) Date of Patent: *Aug. 24, 2004

(54) CLEANSING COMPOSITIONS WITH MILK PROTEIN AND AROMATHERAPY

(75) Inventors: Catherine A. Piterski, River Vale, NJ (US); Grace Riccardi, Hoboken, NJ (US)

(73) Assignee: Playtex Products, Inc., Westport, CT (US)

( * ) Notice: Subject to any disclaimer, the term of this patent is extended or adjusted under 35 U.S.C. 154(b) by 17 days.

This patent is subject to a terminal disclaimer.

(21) Appl. No.: 10/097,057

(22) Filed: Mar. 13, 2002

(65) Prior Publication Data

US 2002/0177535 A1 Nov. 28, 2002

Related U.S. Application Data

(63) Continuation-in-part of application No. 10/067,187, filed on Feb. 4, 2002.
(60) Provisional application No. 60/266,828, filed on Feb. 6, 2001.

(51) Int. Cl.$^7$ .............................. C11D 1/14; C11D 1/94; C11D 3/26; C11D 3/50
(52) U.S. Cl. ....................... 510/124; 510/119; 510/123; 510/125; 510/126; 510/127; 510/130; 510/137; 510/158; 510/159; 510/101; 510/504; 510/138; 424/70.11; 424/70.19; 424/70.21; 424/70.22; 424/70.24; 424/70.27; 424/70.28; 424/70.31
(58) Field of Search ................................ 510/119, 123, 510/124, 125, 126, 127, 130, 137, 138, 158, 159, 101, 504; 424/70.11, 70.19, 70.21, 70.22, 70.24, 70.27, 70.28, 70.31

(56) References Cited

U.S. PATENT DOCUMENTS

| | | | |
|---|---|---|---|
| 4,243,659 A | 1/1981 | Balingit et al. | 424/70 |
| 4,631,187 A | 12/1986 | Padden et al. | 424/70 |
| 5,096,608 A | 3/1992 | Small et al. | 252/132 |
| 5,221,530 A | 6/1993 | Janchitraponvej et al. | 424/70 |
| 5,290,471 A | 3/1994 | Greene et al. | 252/108 |
| 5,290,482 A | 3/1994 | Marschner et al. | 252/544 |
| 5,391,368 A | 2/1995 | Gerstein | 424/70.13 |
| 5,478,490 A | 12/1995 | Russo et al. | 252/153 |
| 5,525,263 A | 6/1996 | Bimczok et al. | 252/551 |
| 5,632,978 A | 5/1997 | Moore et al. | 510/159 |
| 5,681,546 A | 10/1997 | Lee et al. | 424/45 |
| 5,681,802 A | 10/1997 | Fujiwara et al. | 510/130 |
| 5,720,961 A | 2/1998 | Fowler et al. | 424/401 |
| 5,785,979 A | 7/1998 | Wells | 424/401 |
| 5,858,938 A | 1/1999 | Glenn, Jr. et al. | 510/130 |
| 5,880,299 A | 3/1999 | Ponsati Obiols et al. | 554/109 |
| 5,883,058 A | 3/1999 | Wells et al. | 510/127 |
| 5,883,068 A | 3/1999 | Hensen et al. | 510/427 |
| 5,910,472 A | 6/1999 | Elliott | 510/124 |
| 5,916,586 A | 6/1999 | Villa et al. | 424/443 |
| 5,925,603 A | 7/1999 | D'Angelo | 510/119 |
| 5,925,615 A | 7/1999 | Kern et al. | 510/463 |
| 5,925,747 A | 7/1999 | Uphues et al. | 536/18.5 |
| 5,942,238 A | 8/1999 | McAtee et al. | 424/401 |
| 5,951,991 A | 9/1999 | Wagner et al. | 424/401 |
| 5,972,361 A | 10/1999 | Fowler et al. | 424/402 |
| 5,977,036 A | 11/1999 | Guskey | 510/121 |
| 5,993,792 A * | 11/1999 | Rath et al. | 424/70.28 |
| 6,001,339 A | 12/1999 | Finel et al. | 424/70.12 |
| 6,017,861 A | 1/2000 | Fujiwara et al. | 510/130 |
| 6,022,547 A | 2/2000 | Herb et al. | 424/401 |
| 6,034,043 A | 3/2000 | Fujiwara et al. | 510/130 |
| 6,040,282 A | 3/2000 | Guskey et al. | 510/119 |
| 6,043,202 A | 3/2000 | Eriksen et al. | 510/119 |
| 6,043,204 A | 3/2000 | Kaufman et al. | 510/130 |
| 6,063,397 A | 5/2000 | Fowler et al. | 424/443 |
| 6,074,655 A | 6/2000 | Fowler et al. | 424/402 |
| 6,086,903 A | 7/2000 | Trinh et al. | 424/401 |
| 6,087,320 A | 7/2000 | Urfer et al. | 510/470 |
| 6,132,746 A | 10/2000 | Hasenoehrl et al. | 424/402 |
| 6,153,208 A * | 11/2000 | McAtee et al. | 424/402 |
| 6,162,774 A | 12/2000 | Charlton et al. | 510/130 |
| 6,165,454 A | 12/2000 | Patel et al. | 424/70.11 |
| 6,165,955 A | 12/2000 | Chen et al. | 510/123 |
| 6,190,678 B1 * | 2/2001 | Hasenoehrl et al. | 424/401 |
| 6,204,229 B1 | 3/2001 | Hasegawa et al. | 510/101 |
| 6,284,230 B1 * | 9/2001 | Sako et al. | 424/70.11 |
| 6,287,583 B1 * | 9/2001 | Warren et al. | 424/404 |
| 6,358,516 B1 * | 3/2002 | Harod | 424/401 |
| 6,372,334 B1 * | 4/2002 | Wycech | 428/316.6 |
| 6,451,333 B1 * | 9/2002 | Beerse et al. | 424/405 |
| 6,494,920 B1 * | 12/2002 | Weuthen et al. | 8/137 |
| 6,495,498 B2 * | 12/2002 | Niemiec et al. | 510/122 |
| 6,506,713 B1 * | 1/2003 | Slavtcheff et al. | 510/130 |
| 6,566,313 B1 * | 5/2003 | Hohenstein et al. | 510/125 |
| 2002/0151446 A1 * | 10/2002 | Piterski et al. | 510/130 |

FOREIGN PATENT DOCUMENTS

| | | | |
|---|---|---|---|
| WO | WO 98/24401 | * | 6/1998 |
| WO | WO 98/29094 | * | 7/1998 |

OTHER PUBLICATIONS

"International Cosmetic Ingredient Dictionary and Handbook", 9$^{th}$ Edition 2002, vol. 1, by the Cosmetic, Toiletry, and Fragrance Association.

* cited by examiner

Primary Examiner—Gregory R. Del Cotto
(74) Attorney, Agent, or Firm—Ohlandt, Greeley, Ruggiero & Perle, LLP

(57) ABSTRACT

A mild foaming cleanser composition is provided. The cleanser composition has a surfactant system, a moisturizer system, an aromatherapy system and a solvent system. The moisturizer system further includes a milk protein. In addition, the cleanser composition may also include an emulsifier, preservative, pH adjusting agent, thickening agent, emollient, opacifying agent, fragrance, or any combinations thereof.

47 Claims, No Drawings

CLEANSING COMPOSITIONS WITH MILK PROTEIN AND AROMATHERAPY

RELATED APPLICATION

This application is a Continuation-In-Part of U.S. application Ser. No. 10/067,187, filed on Feb. 4, 2002, which claims priority from U.S. Provisional Patent Application Serial No. 60/266,828, filed on Feb. 6, 2001.

BACKGROUND OF THE INVENTION

1. Field of the Invention

The present invention relates to cleansing compositions. More particularly, the present invention relates to cleansing compositions for infant and toddler use that have a moisturizer system containing a milk protein for nourishing the skin and an aromatherapy system for promoting calming effect to the user.

Typically, baby cleansers have a fairly high level of one or more mild cleansing agents. However, many cleansers clean skin and hair at the expense of drying out or stripping moisture from the skin and/or hair. A conditioner may be included in the cleanser composition for conditioning the skin and/or hair. Most conditioning agents are substantive. Substantive agents adhere to the skin to provide a conditioning effect, thereby causing irritation to sensitive membranes, such as those found in the eye. Thus, substantive compositions are not desirable for use in compositions used for bathing infants or toddlers.

One focus of the subject compositions is to avoid concerns involved with cleansing formulations, such as drying and tearing. The subject compositions distinguish over prior cleansing formulations because not only do they effectively cleanse, but they are also mild, less drying to the skin, tear free, and, in addition, nourish and moisturize the skin.

Another focus of the subject compositions is to make bathing an infant or toddler less stressful for both the caregiver and for the infant. Many infants are fussy and uncomfortable in the bath. This can make the bath time very difficult for the caregiver. The subject compositions further distinguish over prior cleansing formulations because they contain an added aromatherapy system. Aromatherapy has been used since ancient times to reduce stress, relax, uplift, and restore emotional well-being. The addition of an aromatherapy system to such cleansing compositions may act to promote a calming effect on the infant during and after the bath.

2. Description of the Prior Art

The favorable effect of milk or products derived from milk on cosmetic compositions, such as lotions for the skin, hair lotions, shampoos, softening creams, and soaps, is well known. Numerous compositions containing such ingredients have been described in the state of the art.

U.S. Pat. No. 3,959,491 discloses cosmetic creams and lotions containing sterilized milk and milk cream. To improve the preservation of such products in storage, a saturated fatty acid, triglyceride esters of saturated fatty acid, stabilizing aliphatic diol, sequestering agent and biocidal agent, in particular enzyme denaturant and bactericide, are incorporated into the cosmetic compositions. The cosmetics disclosed also contain the usual constituents of cosmetics, including a perfume, opacifier and others.

U.S. Pat. No. 4,460,571 discloses a cosmetic composition, including a lotion, with whole or powdered milk, which particularly lends itself to topodermic and capillary uses.

GB 2,056,854 discloses cosmetics, in particular a lotion and shampoo, containing, apart from the normal ingredients inherent in such products, very high proportions of milk (40-80%) and, as a stabilizing agent, propylene glycol.

GB 2,037,160 discloses a lyophilized product derived from milk having advantageous cosmetic properties, in particular for moisturizing and softening of the skin along with its regeneration. The lyophilized product is used, in a mixture, with a cosmetic composition to improve their properties.

DE 2,623,250 discloses cosmetic compositions, such as, shampoo, beauty lotion, shaving cream, and cream for the skin, containing milk. All of these products have in common, apart from milk and water, a surfactant substance, such as alkyl-sulfonate, sulfonated fatty acid, and the salts of tertiary amines, etc. The milk may be present in the form of whole milk, low fat milk, acidified milk, skimmed milk, yogurt, cream, etc. in aqueous form or in a powder. Furthermore, the compositions described may also contain, depending on the use for which they are intended, other ingredients such as lanolin, perfume, glycerin and other similar products.

DE 2,650,560 discloses cosmetic compositions containing milk in the form of yogurt. This milk is usable in the fresh state or in a powder. Among such cosmetic or cosmetic compositions, this application discloses liquid and solid products, in particular a beauty milk, cream, and aerosol for foam. These compositions contain, apart from yogurt, a preservative, antioxidant, chelator, and protease inhibitor.

U.S. Pat. No. 5,053,219 discloses cosmetic products containing a milk constituent, such as natural milk proteins in the form of micelles formed by the addition of calcium to an aqueous solution of casein. These micelles give the product light reflection properties analogous to those produced by the addition of a natural milk.

U.S. Pat. No. 5,314,873 discloses milk protein hydrolyzates and compositions for use as hair and skin treating agent. The milk protein hydrolyzate includes a mixture of peptide and free amino acid. The milk protein hydrolyzate is obtained by enzymatic hydrolysis of milk protein.

Aromatherapy and its various uses has been described in the prior art. U.S. Pat. No. 5,888,984 discloses a topical pharmaceutical composition of complex carbohydrate and essential oil. The composition reduces inflammation, assists in wound healing, protects against bruising, relieves itching, relieves pain and swelling and treats topical bacterial infections, such as acne.

U.S. Pat. No. 6,280,751 discloses medicinal and cosmetic compositions having essential oils in combination with herbs and/or spices. The compositions include topical compositions.

What is not appreciated by the prior art is a cleansing composition that simultaneously moisturizes the skin while promoting calming and healing of the user by aromatherapy. The present lotion composition overcomes this deficiency by providing a moisturizing lotion composition with one or more milk protein compounds and one or more essential oils.

SUMMARY OF THE INVENTION

It is an object of the present invention to provide mild cleanser compositions for use in bathing infants or toddlers.

It is another object of the present invention to provide such cleanser compositions that are tear free.

It is a yet another object of the present invention to provide such cleanser compositions that are non-drying to the skin.

It is a still another object of the present invention to provide such cleanser compositions that moisturize and condition the skin.

It is a still another object of the present invention to provide such cleanser compositions with a moisturizer system that contains a milk protein.

It is a further object of the present invention to provide such cleanser compositions that promote a calming effect and overall enhancement of the mood of the bather.

It is a still further object of the present invention to provide such cleanser compositions that have an aromatherapy component that promotes a calming effect and overall enhancement of the mood of the bather.

These and other objects and advantages of the present invention are achieved by the mild foaming cleanser compositions according to the present invention. The cleanser compositions have a surfactant system, a moisturizer system, an aromatherapy system. Preferably, the cleanser compositions also have a solvent or solvent system. In addition, the cleanser compositions may also include emulsifier, preservative, pH adjusting agent, thickening agent, emollient, opacifying agent, fragrance, or any combinations thereof.

DETAILED DESCRIPTION OF THE INVENTION

The present invention is one or more cleansing or cleanser compositions for an infant or toddler that can be used for the body, the hair, or both. The compositions have advantages over cleansing compositions currently available in the market. For example, the present compositions provide gentle, tear free cleansing of the skin and hair, improve the moisture content and condition of the skin, and promote relaxation of the user. Tear free cleansing, skin conditioning, and a reduction of drying effect to the skin are primarily due to the presence of a mild surfactant system and a moisturizer system that contains a milk protein. The calming effect is primarily due to the presence of an aromatherapy system in the composition.

The compositions of the present invention have a surfactant or a surfactant system, a moisturizer system, a solvent system and an aromatherapy system. In one embodiment of the present invention the cleansing composition may be dispensed in a liquid form. An important aspect of the present invention is that the composition is a thin liquid that allows for easy coverage and dispersal of the composition on the body and hair. In this form, the cleansing composition is readily added the hand or to a cloth for application to an infant or toddler. The liquid cleanser composition contains a thickener, an emollient and an opacifying agent.

In an alternate embodiment of the present invention, the cleansing composition is a thin liquid formulation that dispenses as a thick, rich foam. In this embodiment, a no-drip dispenser is used to generate the desired foaming characteristics of the present composition. Namely, a foam provides extra assurance against eye irritation because a foam does not readily move along the skin.

The compositions of the present invention have a surfactant or surfactant system that is relatively mild. Mild surfactants are those known in the art to be non-irritating to the skin and eyes. Moreover, a mild surfactant or surfactant system does not strip the skin of moisture. Suitable surfactants for use in the surfactant system include, for example, amphoteric, anionic, cationic, nonionic, zwitterionic, or any combinations thereof.

The compositions have a lower active amount of mild surfactant system than is typically found in baby cleansing compositions. This lower amount of surfactant results in less skin irritation and allows for greater moisture retention and less drying of the skin. Also, this low amount allows the composition to be a very thin liquid. However, despite the low amount of surfactant, a rich foam composition is achieved that is effective at cleansing the body and hair.

The surfactant or surfactant system is about 0.1 percentage by weight (wt. %) to about 27 wt. % of the total weight of the compositions of the present invention. In a preferred embodiment, the surfactant is about 5 wt. % to about 14 wt. %. In a more preferred composition of the present invention, the surfactant is present in an amount about 9 wt. % to about 13 wt. % of the total weight of the composition.

Suitable anionic surfactants may include, for example, one or more alcohol sulfates, alcohol sulfonates, alcohol phosphates, alcohol phosphonates, alkyl sulfates, alkyl sulfonates, alkylaryl sulfates, alkylaryl sulfonates, alkali metal salts of fatty acids, ammonium salts of fatty acids, sulfonated amines, sulfonated amides, fatty sarcosinates, linear alkylated sulfonates, alcohol ether sulfates, secondary alkane sulfonates, or any combinations thereof. Preferred anionic surfactants for use in the present invention, include, for example, sodium laureth sulfate, sodium lauroyl ethylenediaminetriacetate (ED3A), or any combinations thereof.

Anionic surfactant is present in the liquid bath embodiment of the cleansing composition in an amount about 0.1 wt. % to about 10 wt. % of the total weight of the composition. Preferably, anionic surfactant is present in an amount about 1 wt. % to about 8 wt. %.

Anionic surfactant is present in the foaming embodiment of the cleansing composition in an amount about 0.1 wt. % to about 10 wt. % of the total weight of the composition. Preferably, anionic surfactant is present in an amount about 1 wt. % to about 5 wt. %.

Suitable nonionic surfactants that can be used in the cleaning compositions of the present invention include, for example, one or more alkoxylated alcohols, ethoxylated (EO) alcohols, propoxylated (PO) alcohols, inter-dispersed ethoxylated-propoxylated (EO-PO) alcohols, copolymers, fatty acids, alkyl phenols, polyglycosides, polyglucosides, n-alkylpyrrolidones, block copolymers, or any combinations thereof. Preferred nonionic surfactants include, for example, PEG-30 glyceryl cocoate, PEG-80 glyceryl cocoate, decyl glucoside, or any combinations thereof.

The nonionic surfactant is present in the liquid bath embodiment of the cleansing composition in an amount about 0.5 wt. % to about 14 wt. % of the total weight of the composition. Preferably, the nonionic surfactant is present in an amount about 5 wt. % to about 12 wt.

The nonionic surfactant is present in the foaming embodiment of the cleansing composition in an amount about 0.5 wt. % to about 12 wt. % of the total weight of the composition. Preferably, the nonionic surfactant is present in an amount about 5 wt. % to about 10 wt. %.

Suitable amphoteric surfactants include, for example, one or more betaines, amine oxides, fatty amine oxides, alkyl amine oxides, or any combinations thereof. Preferred amphoteric surfactant include, for example, one or more betaines, such as, cocamidopropyl betaine. The betaine surfactant also provides foam boosting properties to the composition, which avoids the need for further foam booster.

Significantly, the total activity or percent solids contributed by the surfactant or surfactant system in the liquid bath embodiment of the cleansing composition is less than 27 wt. % of the total weight and, preferably, less than 20 wt. %. The total activity or percent solids contributed by the surfactant or surfactant system in the foaming embodiment of the cleansing composition is less than 17 wt. % of the total weight and, preferably, less than 15 wt. %. This ensures that the composition is mild and thus, non-irritating to the infant or toddler.

The amphoteric surfactant is present in the liquid bath embodiment of the cleansing composition in an amount about 0.1 wt. % to about 5 wt. % of the total weight of the composition, and preferably, in an amount about 1 wt. % to about 4 wt. %. The amphoteric surfactant is present in the foaming embodiment of the cleansing composition in an amount about 0.1 wt. % to about 5 wt. % of the total weight of the composition, and preferably, in an amount about 1 wt. % to about 4 wt. %.

The compositions also have a moisturizer or moisturizer system. The choice of moisturizer for use in the moisturizer system is predicated on a combination of the following two factors, low irritation potential and skin moisture level preservation. Also, the moisturizer does not thicken the composition, since thickening would be contrary to the desired thin liquid composition of the present invention.

The moisturizer system of the present invention has a hydrolyzed milk protein and a moisturizer. Suitable moisturizers that can be used in the moisturizer system may include, for example, one or more amidoamine salts, lactic acid salts, sunflowerseed amidopropyl dimethylamine lactate (MACKALENE 1216), isostearamidopropyl morpholine lactate (MACKALENE 426), sodium $C_{12}$–$C_{15}$ alkoxypropyl iminodiproprionate and laureth-12 sulfosuccinate (CETYLSIL NS), cocoglucoside and glyceryl oleate (LAMESOFT PO 65), casteryl maleate (CERAPHYL RMT), olive oil, glycerin, aloe, or any combinations thereof. Preferably, the moisturizer system includes sunflowerseed amidopropyl dimethylamine lactate (MACKALENE 1216), glycerin, or any combinations thereof.

As stated above, the moisturizer system of the present compositions also has at least one milk protein and/or milk protein hydrolysate. The milk protein serves as a cationic conditioning agent for the skin and hair. The at least one milk protein compound in the composition of the present invention has been found to enhance the moisturizing of the skin. Suitable milk protein compounds for use in the present invention include, for example, hydrolyzed milk protein, hydrolyzed milk protein derivative, or any combinations thereof. Suitable hydrolyzed milk protein derivatives include, for example, palmitoyl derivative and quaternary ammonium salt derivative. Preferably, the milk protein used in the present lotion composition is a hydrolyzed milk protein sold under the tradename Hydrolactin 2500® by Croda, Inc.

To achieve enhanced moisturizing properties, the moisturizer system is present in the composition of the present invention in an amount about 0.01 wt. % to about 6 wt. % of the total weight of the composition. Preferably, the moisturizer system is present in an amount about 3 wt. % to about 4 wt. %. The milk protein is preferably present in the composition in an amount about 0.001% to about 1% while the moisturizer is preferably present in an amount about 0.01 wt. % to about 0.5% of the total weight of the composition.

The composition also has an aromatherapy component. Aromatherapy has been used for centuries as a way to promote physical and mental well being. Essential oils extracted from flowers, herbs, spices, woods, and fibers, when inhaled, are believed to have subtle effects on a person's mind and emotions. In addition, it is believed that when the essential oils penetrate the skin and enter the bloodstream and immune system, they work in a physiological manner to promote healing.

Essential oils are highly scented droplets found in minute quantities in the flowers, stems, leaves, roots and barks of aromatic plants. They are highly fluid and exceptionally volatile and potent. Because of their high potency, very small amounts of essential oil are needed to experience their benefits.

Essential oils are complex mixtures of different organic molecules, such as terpenes, alcohols, esters, aldehydes, ketones and phenols. It is believed that it is the interaction between each and every component and/or molecule that gives an essential oil its particular character and unique therapeutic properties. Therefore, the use of one or more essential oils in the present lotion composition not only provides a calming effect to the infant, it may also provide beneficial healing effects.

A variety of essential oils may be used for the present invention. Suitable essential oils for use in the present lotion composition include, for example, Abies Sibirica Oil, Amyris Balsamifera Oil, Anise (Illicium Verum) Oil, Balm Mint (Melissa Officinalis) Oil, Basil (Ocimum Basilicum) Oil, Bay (Pimenta Acris) Oil, Bee Balm (Monarda Didyma) Oil, Bergamot (Citrus Aurantium Bergamia) Oil, Birch (Betula Aba) Oil, Bitter Orange (Citrus Aurantium Amara) Oil, Cabbage Rose (Rosa Centifolia) Oil, Calendula Officinalis Oil, California Nutmeg (Torreya Californica) Oil, Camellia Sinensis Oil, Capsicum Frutescers Oleoresin, Caraway (Carum Carvi) Oil, Cardamon (Elettaria Cardamomum) Oil, Cedarwood (Cedrus Atlantica) Oil, Chamaecyparis Obtusa Oil, Chamomile (Anthemis Nobilis) Oil, Cinnamon (Cinnamomum Cassia) Oil, Citronella (Cymbopogon Nardus) Oil, Clary (Salvia Sclarea) Oil, Clove (Eugenia Caryophyllus) Oil, Cloveleaf (Eugenia Caryophyllus) Oil, Coriander (Coriandrum Sativum) Oil, Coriander (Coriandrum Sativum) Seed Oil, Cyperus Esculentus Oil, Cypress (Cupressus Sempervirens) Oil, Eucalyptus Citriodora Oil, Eucalyptus Globulus Oil, Fennel (Foeniculum Vulgare) Oil, Gardenia Florida Oil, Geranium Maculatum Oil, Ginger (Zingiber Officinale) Oil, Gold of Pleasure (Camelina Sativa) Oil, Grapefruit (Citrus Grandis) Oil, Hops (Humulus Lupulus) Oil, Hypericum Perforatum Oil, Hyptis Suaveolens Oil, Indigo Bush (Dalea Spinosa) Oil, Jasmine (Jasminum Officinale) Oil, Juniperus Communis Oil, Juniperus Virginiana Oil, Labdanum (Cistus Labdaniferus) Oil, Laurel (Laurus Nobilis) Oil, Lavandin (Lavandula Hybrida) Oil, Lavender (Lavandula Angustifolia) Oil, Lemon (Citrus Medica Limonum) Oil, Lemongrass (Cymbopogon Schoenanthus) Oil, Leptospermum Scoparium Oil, Lime (Citrus Aurantifolia) Oil, Linden (Tilia Cordata) Oil, Litsea Cubeba Oil, Lovage (Levisticum Officinale) Oil, Mandarin Orange (Citrus Nobilis) Oil, Massoy Bark Oil, Matricaria (Chamomilla Recutita) Oil, Moroccan Chamomile Oil, Musk Rose (Rosa Moschata) Oil, Myrrh (Commiphora Myrrha) Oil, Myrtle (Myrtus Communis) Oil, Norway Spruce (Picea Excelsa) Oil, Nutmeg (Myristica Fragrans) Oil, Olax DissitifloraOil, Olibanum, Opoponax Oil, Orange (Citrus Aurantium Dulcis) Flower Oil, Orange (Citrus Aurantium Dulcis) Oil, Palmarosa (Cymbopogon Martini) Oil, Parsley (Carum Petroselinum) Seed Oil, Passionflower (Passiflora Incarnata) Oil, Patchouli (Pogostemon Cablin) Oil, Pelargonium Graveolens Oil, Pennyroyal (Mentha Pulegium) Oil, Peppermint (Mentha Piperita) Oil, Pine (Pinus Palustris) Oil, Pine (Pinus Palustris) Tar Oil, Pine (Pinus Pinea) Kernel Oil, Pine (Pinus Pumiho) Oil, Pine (Pinus Sylvestris) Cone Oil, Rosemary (Rosmarinus Officinalis) Oil, Rose Oil, Rosewood (Aniba Rosseodora) Oil, Rue (Ruts Graveolens) Oil, Sage (Salvia Officinalis) Oil, Sambucus Nigra Oil, Sandalwood (Santalum Album) Oil, Sandarac (Callitris Quadrivalvis) Gum, Sassafras Officinale Oil, Sisymbrium Ino Oil, Spearmint (Mentha Viridis) Oil, Sweet Marjoram (Origanum Majorana) Oil, Sweet Violet (Viola Odorata) Oil, Tar Oil, Thuja Occidentalis Oil, Thyme (Thymus Vulgaris) Oil, Vetiveria Zizanoides Oil, Wild Mint (Mentha Arvensis) Oil, Ximenia Americana Oil, Yarrow (Achillea Millefolium) Oil, Ylang Yang (Cananga Odorata) Oil, or any combinations thereof.

The preferred essential oils for use in the present invention are lavendin and chamomile. Lavendin, a botanical variety of lavender, is used for promoting relaxation and calming effect to the bather. Chamomile is used for promoting calm and relaxation to the bather.

As used in the present invention, the one or more essential oils are present in an amount about 0.00001 wt. % to about 1 wt. %, based on the total weight of the composition. Preferably, the one or more essential oils are present in an amount about 0.00005 wt. % to about 0.1 wt. %, and more preferably about 0.0001 wt. % to about 0.015 wt. % of the total weight of the composition.

In particular, the aromatherapy component of the cleansing compositions includes the oils lavendin and chamomile. The aromatherapy component lavendin is present in an amount about 0.00005 wt. % to about 0.1 wt. % of the total weight of the composition. The aromatherapy component chamomile is present in an amount about 0.00005 wt. % to about 0.1 wt. % of the total weight of the composition.

One aspect in achieving the thin liquid composition of the present invention, is the inclusion of a solvent or solvent system in the composition. Suitable solvents for use in the system include, for example, water, alcohol, polyhydric alcohol, glycerin, glycol, or any combinations thereof. Preferably, the solvent is water.

The solvent or solvent system is present in the composition in an amount about 75 wt. % to about 98 wt. % based on the total weight of the composition. Preferably, the solvent is present in an amount about 80 wt. % to about 90 wt. %.

The composition can also include one or more additional components. Suitable additional components may include, for example, foam booster other than betaine amphoteric surfactant earlier discussed, emulsifier, humectant, preservative, chelating agent, conditioner, pH adjuster, thickening agent, emollient, opacifying agent, perfume and/or fragrance, or any combinations thereof.

The composition of the present invention may also have a mild foam booster, in addition to the betaine amphoteric surfactant described before. Suitable mild foam boosters include, for example, one or more amides, sulfosuccinates, or any combinations thereof. The mild foam booster, when present in the composition, is present in a minimal amount. The amount of foam booster is about 0.1 wt. % to about 6 wt. % of the total weight of the composition. Preferably, the amount of foam booster is about 0.5 wt. % to about 5 wt. % of the total weight of the composition. More preferably, the amount of foam booster is about 1 wt. % to about 4 wt. %.

Any mild emulsifier that meets the criteria set forth above may be used in the present composition. Suitable emulsifiers that can be used in the present invention include, for example, one or more sorbitans, alkoxylated fatty alcohols, alkylpolyglycosides, soaps, alkyl sulfates, monoalkyl and dialkyl phosphates, alkyl sulphonates, acyl isothionates, or any combinations thereof. A preferred emulsifier is polysorbate 20. This particular emulsifier also serves to solubilize any fragrance and/or perfume present in the composition.

When used in the present composition, the emulsifier is about 0.1 wt. % to about 2 wt. % of the total weight of the composition. More preferably, emulsifier is present in an amount about 0.5 wt. % to about 1.5 wt. % of the total weight of the composition.

The composition may, optionally, include humectant. A humectant is a component that absorbs or retains moisture. Suitable humectants that can be used in the present composition include, for example, urea, pyroglutamic acid, amino acid, polyol or other compounds with hygroscopic properties, or any combinations thereof.

When present, the humectant is in an amount about 1 wt. % to about 5 wt. %, and preferably about 2 wt. % to about 4 wt. %, of the total weight of the composition. More preferably, the humectant is present in an amount about 2.5 wt. % to about 3.5 wt. % of the total weight of the composition.

The composition may, optionally, have a preservative or preservative system. Suitable preservatives for use in the present compositions include one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof. Preferably, the preservative system includes propylene glycol, diazolidinyl urea, methylparaben, propylparaben or any combinations thereof. More preferably, the preservative system has a combination of propylene glycol, diazolidinyl urea, methylparaben, and propylparaben. Such a preferred combination is sold under the trade name GERMABEN II by International Specialty Products.

When present, the preservative or preservative system is in an amount about 0.1 wt. % to about 1.5 wt. % of the total weight of the composition. Preferably, the preservative is in an amount about 0.3 wt. % to 1.2 wt. % of the total weight of the composition.

The composition may additionally include a chelating agent to enhance the preservative or preservative system. The chelating agent should be mild, such as, for example, ethylenediaminetetraacetic acid (EDTA), one or more EDTA derivatives, or any combinations thereof.

The chelating agent is present in an amount about 0.1 wt. % to about 5 wt. %, and preferably about 2 wt. % to about 4 wt. %, of the total weight of the composition.

The composition may also optionally include a hair conditioner. The hair conditioner should be mild. Suitable hair conditioners that can be used in the present composition include, for example, one or more collagens, proteins, keratins, dimethicone polyols, quaternary ammonium compounds, halogenated quaternary ammonium compounds, alkoxylated carboxylic acids, alkoxylated alcohols, alkoxylated amides, sorbitan derivatives, esters, polymeric ethers, glyceryl esters, or any combinations thereof.

The hair conditioner, when present, is in an amount about 0.01 wt. % to about 5 wt. % of the total weight of the composition. Preferably, the hair conditioner is present in an amount about 0.1 wt. % to about 2 wt. % of the total weight of the composition.

The composition may also optionally include a pH adjuster. Suitable pH adjusters include, for example, one or more adipic acids, glycines, citric acids, calcium hydroxides, magnesium aluminometasilicates, or any combinations thereof. The pH adjuster is added to maintain desired pH levels. Preferably, citric acid is used as the pH adjuster. If present, the pH adjuster is about 0.001 wt. % to about 1 wt. %, and preferably about 0.01 wt. % to about 0.5 wt. %, of the total weight of the composition. The pH of the composition of the present invention is about 4 to about 9. Preferably, the pH is about 5.5 to about 7.5.

The liquid bath embodiment of the cleansing composition may additionally include a thickening agent to obtain a desired consistency of the cleansing composition. Suitable thickening agents include: gum thickeners, such as xanthan gum and guar gum; water soluble polymers, such as methylcellulose, ethylcellulose, hydroxyethylcellulose, hydroxypropylcellulose, hydroxybutylcellulose, hydroxypropyl methylcellulose, hydroxypropyl chitosan, hydroxypropyl guar carbomers, acrylates crosspolymers, acrylates and copolymers; silicates, such as bentonite, magnesium aluminum silicate; salts, such as ammonium chloride, sodium chloride; and surfactants, such as betaines, hydroxysultaines, alkanolamides, amine oxides and hylauronic acid. Preferably, the thickening agent is PEG 120 methyl glucose dioleate or PEG 150 distearate, or any combination thereof. The thickening agent, when present in the composition, is present in an amount about 0.1 wt. % to about 5 wt. %, and preferably about 1 wt. % to about 3 wt. %, of the total weight of the composition.

The composition may additionally include an emollient for softening the skin. Suitable emollients for use in the present lotion composition include, for example, one or more fats and oils, such as, coconut oil and cocoa butter, esters, such as, tricapryl citrate, or any combinations thereof. Preferably, the one or more emollients are coconut oil, cocoa butter, tricapryl citrate, PEG 7 glyceryl cocoate or any combinations thereof.

The emollient, when present in the composition, is present in an amount about 0.1 wt. % to about 10 wt. %, and preferably about 0.5 wt. % to about 5 wt. %, of the total weight of the composition.

The composition may additionally include an opacifying agent for imparting a milky texture to the cleansing composition. The opacifying agent may be a styrene or accylate copolymer. Such styrene or accylate copolymers may include cetearyl alcohol, cetyl alcohol, glycol distearate, hydrogenated olive oil, titanium dioxide and magnesium aluminum silicate. Dermocloud 285, manufactured by Alzo is a preferred opacifying agent.

The opacifying agent, when present in the composition, is present in an amount about 0.1 wt. % to about 3 wt. %, and preferably about 0.5 wt. % to about 2 wt. %, of the total weight of the composition.

The composition may include one or more perfumes and/or fragrances. Only suitably gentle perfumes and fragrances should be used in the composition. The composition may also include one or more colorants.

Example 1 represents the liquid bath composition according to the present invention, as well as a preferred range for each ingredient listed.

EXAMPLE 1

Liquid Bath Composition

COMPOSITION #1

| Ingredient | Range (wt. %) | Purpose |
| --- | --- | --- |
| DI water | QS | solvent |
| Citric acid | 0.01–0.2 | pH adjuster |
| PEG 120 methyl glucose dioleate | 1–2 | thickener |
| Cocoamidopropyl betaine, 30% | 1–5 | secondary surfactant, foam booster, amphoteric |
| Sodium laureth sulfate, 26% | 4–7 | primary surfactant, anionic |
| PEG-30 and PEG-80 glyceryl cocoate | 8–14 | secondary surfactant, glyceryl ester |
| Glycerin | 1–5 | humectant, moisturizer |
| PEG 7 glyceryl cocoate | 0.5–4 | emollient |
| Methyl paraben | NA | preservative |
| Propyl paraben | NA | preservative |
| Polyquaternium 7 | 0.5–3 | cationic conditioning agent |
| Imidazolidinyl urea | NA | Preservative |
| Quaternium-79 hydrolyzed milk protein | 0.01–0.5 | cationic conditioning agent |
| Aloe gel | 0.1–1 | biological additive |
| Styrene/accylate copolymer Tradename Dermocloud 285 | 0.75–1.5 | opacifying agent |
| Aromatherapy and Fragrance | 0.2–0.4 | fragrance |

The above composition is formulated by first heating DI water to about 170° F. The pH adjuster, paraben preservative, and thickener are then dissolved into the heated water. The surfactant and moisturizer are then added to the heated water and mixed until clear. The temperature of the solution is allowed to cool to about 115° F. and opacifier and urea preservative are added. The temperature of the resulting solution is again allowed to cool to about 95° F. and the emulsifier, aromatherapy and fragrance are added and mixed until clear. Finally, the preservative is added to the solution to form the composition.

Example 2 represents the foaming composition according to the present invention, as well as a preferred range for each ingredient listed.

EXAMPLE 2

Foam Composition

| Ingredient | Range (wt. %) | Purpose |
| --- | --- | --- |
| DI water | QS | solvent |
| Citric acid | 0.001–0.1 | pH adjuster |
| cocamidopropyl betaine, 30% | 0.1–3 | amphoteric surfactant |
| Sodium laureth sulfate, 26% | 0.1–2 | anionic surfactant |
| PEG-30 and PEG-80 glyceryl cocoate | 1–9 | nonionic surfactant |
| Glycerin | 1–5 | moisturizer |
| Sunflowerseedamidopropyl dimethylamine lactate, 25% | 0.1–0.5 | moisturizer |
| Methyl paraben | 0.05–0.2 | preservative |
| Propyl paraben | 0.01–0.1 | preservative |
| Decyl glucoside, 50% | 0.5–2 | nonionic surfactant |
| Quaternium-79 hydrolyzed milk protein | 0.01–0.5 | Film foamer, moisturizer |
| Aloe gel | 0.1–1 | Biological additive |
| Imidazolidinyl urea | 0.1–0.5 | preservative |
| Polysorbate 20 | 0.5–2 | emulsifier |
| Aromatherapy and Fragrance | 0.2–0.4 | fragrance |

The above composition of Example 2 is formulated by first heating DI water to about 170° F. Then, pH adjuster is dissolved into the heated water. The surfactant, moisturizer, and paraben preservative is then added to the heated solution. The temperature of the solution is allowed to cool to about 115° F. and additional DI water and urea preservative is added to the solution. The temperature of the resulting solution is again allowed to cool to about 95° F. and the emulsifier, aromatherapy and fragrance are added.

An example of a suitable foaming dispenser for use with the foaming embodiment of the cleansing composition are those set forth in U.S. Pat. Nos. 5,271,530 and 5,443,569, which are incorporated herein by reference. However, any dispenser that similarly transforms a thin liquid into a foam may be used.

A foam dispersion further avoids the need for large amounts of cleanser components in the composition. The thin liquid base transforms into a rich foam upon dispersing from its package. This transformed foam composition is safe for bathing and shampooing of an infant since the foam does not drip into the infant's or toddler's eyes. Thus, the present composition, due to its thin liquid properties for easy coverage and dispersion, and its dispensing as a foam, provides for cleansing of the hair and body, conditioning of the hair, reduction of dryness to the skin and scalp, and tear free application to the infant or toddler.

The thin liquid composition of the present invention used in the foaming embodiment has a viscosity about 1 centipoise to about 64 centipoise. Preferably, the viscosity is about 10 centipoise to about 30 centipoise, and more preferably about 15 centipoise to about 20 centipoise. The viscosity of the present composition is another important aspect of the invention. As noted above, the thin liquid characteristic of the composition allows for easy coverage and dispersion, and its dispensing as a foam, which enables a tear free application to an infant.

It should be understood that the foregoing description is only illustrative of the present invention. Various alternatives and modifications can be devised by those skilled in the art without departing from the present invention. Accordingly, the present invention is intended to embrace all such alternatives, modifications and variances.

We claim:

1. A cleanser composition comprising:
   a mild surfactant system;
   a moisturizer system in an amount about 0.01 wt % to about 6 wt % of the total weight of the composition;
   a solvent system, and
   an aromatherapy system in an amount about 0.00001 wt % to about 1 wt % of the total weight of the composition,
   wherein the moisturizer system includes a milk protein in an amount about 0.001 wt % to about 1 wt % of the total weight of the composition.

2. The composition of claim 1, wherein said mild surfactant system comprises one or more surfactants selected from the group consisting of amphoteric, anionic, cationic, nonionic, zwitterionic, and any combinations thereof.

3. The composition of claim 1, wherein said mild surfactant system comprises a surfactant selected from the group consisting of amphoteric, anionic, nonionic, and any combinations thereof.

4. The composition of claim 3, wherein said amphoteric surfactant is selected from the group consisting of betaine, amine oxide, fatty amine oxide, alkyl amine oxide, and any combinations thereof.

5. The composition of claim 3, wherein said amphoteric surfactant is a betaine.

6. The composition of claim 3, wherein said anionic surfactant is selected from the group consisting of alcohol sulfate, alcohol sulfonate, alcohol phosphate, alcohol phosphonate, alkyl sulfate, alkyl sulfonate, alkylaryl sulfate, alkylaryl sulfonate, alkali metal salt of fatty acid, ammonium salt of fatty acid, sulfonated amine, sulfonated amide, fatty sarcosinate, linear alkylated sulfonate, alcohol ether sulfate, secondary alkane sulfonate, and any combinations thereof.

7. The composition of claim 3, wherein said anionic surfactant is selected from the group consisting of sodium laureth sulfate, sodium lauroyl ethylenediaminetriacetate, and any combinations thereof.

8. The composition of claim 3, wherein said nonionic surfactant is selected from the group consisting of alkoxylated alcohol, ethoxylated alcohol, propoxylated alcohol, inter-dispersed ethoxylated-propoxylated alcohol, copolymer, fatty acid, alkyl phenol, polyglycoside, polyglucoside, n-alkylpyrrolidone, block copolymer, and any combinations thereof.

9. The composition of claim 3, wherein said nonionic surfactant is selected from the group consisting of alkoxylated alcohol, ethoxylated alcohol, propoxylated alcohol, inter-dispersed ethoxylated-propoxylated alcohol, copolymer, fatty acid, alkyl phenol, polyglycoside, polyglucoside, n-alkylpyrrolidone, block copolymer, and any combinations thereof.

10. The composition of claim 3, wherein said nonionic surfactant is selected from the group consisting of PEG-30 glyceryl cocoate, PEG-80 glyceryl cocoate, decyl glucoside, and any combinations thereof.

11. The composition of claim 1, wherein said moisturizer system comprises one or more moisturizers selected from the group consisting of amidoamine salt, lactic acid salt, sunflowerseed amidopropyl dimethylamine lactate, isostearamidopropyl morpholine lactate, sodium $C_{12}$-$C_{15}$ alkoxypropyl iminodiproprionate, laureth-12 sulfosuccinate, cocoglucoside, glyceryl oleate, casteryl maleate, olive oil, glycerin, and any combinations thereof.

12. The composition of claim 1, wherein said moisturizer system comprises a moisturizer selected from the group consisting of sunflowerseed amidopropyl dimethylamine lactate, glycerin, and any combinations thereof.

13. The composition of claim 1, wherein said moisturizer system is about 3 wt. % to about 4 wt. % of the total weight of the composition.

14. The composition of claim 1, wherein said milk protein is about 0.01 wt % to about 0.5 wt % of the total weight of the composition.

15. The composition of claim 1, wherein said milk protein is quaternium-79 hydrolyzed milk protein.

16. The composition of claim 1, wherein said aromatherapy system includes at least one essential oil.

17. The composition of claim 16, wherein said at least one essential oil is lavendin.

18. The composition of claim 16, wherein said at least one essential oil is chamomile.

19. The composition of claim 17, wherein said lavindin is about 0.0001 wt % to about 0.015 wt % of the total weight of the composition.

20. The composition of claim 18, wherein said chamomile is about 0.0001 wt % to about 0.015 wt % of the total weight of the composition.

21. The composition of claim 1, wherein said solvent system comprises one or more solvents selected from the group consisting of water, alcohol, polyhydric alcohol, glycerin, glycol, and any combinations thereof.

22. The composition of claim 1, wherein said solvent system comprises water.

23. The composition of claim 1, wherein said solvent system is about 75 wt. % to about 98 wt. % of the total weight of the composition.

24. The composition of claim 1, wherein said solvent system is about 80 wt. % to about 90 wt. % of the total weight of the composition.

25. The composition of claim 1, further comprising one or more additional components selected from the group consisting of foam booster other than betaine surfactant, emulsifier, humectant, preservative, chelating agent, conditioner, pH adjuster, perfume, fragrance, aloe gel, thickening agent, emollient, opacifying agent, and any combinations thereof.

26. The composition of claim 25, wherein said emulsifier is selected from the group consisting of sorbitan, alkoxylated fatty alcohol, alkylpolyglycoside, soap, alkyl sulfate, monoalkyl phosphate, dialkyl phosphate, alkyl sulfonate, acyl isothionate, and any combinations thereof.

27. The composition of claim 25, wherein said emulsifier is about 0.1 wt. % to about 2 wt. % of the total weight of the composition.

28. The composition of claim 25, wherein said humectant is selected from the group consisting of urea, pyroglutamic acid, amino acid, polyol, and any combinations thereof.

29. The composition of claim 25, wherein said humectant is about 1 wt. % to about 5 wt. % of the total weight of the composition.

30. The composition of claim 25, wherein said preservative is selected from the group consisting of alkanol, disodium EDTA, EDTA salt, EDTA fatty acid conjugate, isothiazolinone, paraben, propylene glycol, sorbate, urea derivative, and any combinations thereof.

31. The composition of claim 25, wherein said preservative is selected from the group consisting of propylene glycol, diazolidinyl urea, methyl paraben, propylparaben, and any combinations thereof.

32. The composition of claim 25, wherein said preservative is about 0.1 wt. % to about 1.5 wt. % of the total weight of the composition.

33. The composition of claim 25, wherein said pH adjuster is selected from the group consisting of adipic acid, glycine, citric acid, calcium hydroxide, magnesium aluminometasilicate, and any combinations thereof.

34. The composition of claim 25, wherein said pH adjuster is about 0.001 wt. % to about 1 wt. % of the total weight of the composition.

35. The composition of claim 25, wherein said thickening agent is about 1 wt % to about 3 wt. % of the total weight of the composition.

36. The composition of claim 25, wherein said emollient is about 0.5 wt. % to about 5 wt. % of the total weight of the composition.

37. The composition of claim 25, wherein said opacifying agent is about 0.5 wt. % to about 2 wt. % of the total weight of the composition.

38. The composition of claim 1, wherein the composition has a pH about 4 to about 9.

39. The composition of claim 1, wherein the composition is a tear free composition.

40. The composition of claim 1, wherein the composition is a liquid cleanser.

41. The composition of claim 40, wherein said mild surfactant system is about 0.1 wt. % to about 27 wt. % of the total weight of the composition.

42. The composition of claim 40, wherein said mild surfactant system is about 5 wt. % to about 20 wt. % of the total weight of the composition.

43. The composition of claim 40, wherein said mild surfactant system is about 10 wt. % to about 18 wt. % of the total weight of the composition.

44. The composition of claim 1, wherein the composition is delivered as a foam.

45. The composition of claim 44, wherein said mild surfactant system is about 0.1 wt. % to about 15 wt. % of the total weight of the composition.

46. The composition of claim 44, wherein said mild surfactant system is about 5 wt. % to about 14 wt. % of the total weight of the composition.

47. The composition of claim 44, wherein said mild surfactant system is about 9 wt. % to about 13 wt. % of the total weight of the composition.

* * * * *